(12) United States Patent
Boyer (10) Patent No.: US 7,644,478 B2
(45) Date of Patent: Jan. 12, 2010

(54) METHOD OF EMBALMING WITH SAND-FILLED WEIGHTS (75) Inventor: Charles E. Boyer, 724 Main St., Rural Valley, PA (US) 16249

(73) Assignee: Charles E. Boyer, Rural Valley, PA (US)

(*) Notice: Subject to any disclaimer, the term of this patent is extended or adjusted under 35 U.S.C. 154(b) by 793 days.

(21) Appl. No.: 11/146,308

(22) Filed: Jun. 6, 2005

(65) Prior Publication Data
US 2005/0283957 A1 Dec. 29, 2005

Related U.S. Application Data (60) Provisional application No. 60/577,653, filed on Jun. 7, 2004.

(51) Int. Cl.
A01N 1/00 (2006.01)
(52) U.S. Cl. .......................................... 27/22.1; 27/25.1
(58) Field of Classification Search ............... 27/22.1, 27/25.1
See application file for complete search history.

(56) References Cited

U.S. PATENT DOCUMENTS

| 1,934,918 | A |   | 11/1933 | Everson |   |
|---|---|---|---|---|---|
| 2,210,113 | A |   | 8/1940 | Davis |   |
| 2,576,871 | A |   | 11/1951 | Wright |   |
| 2,677,166 | A |   | 5/1954 | Slocum et al. |   |
| 2,709,293 | A | * | 5/1955 | Tucker et al. | 27/21.1 |
| 2,795,838 | A |   | 6/1957 | McNeely |   |
| 2,883,730 | A |   | 4/1959 | Ledoux |   |
| 3,234,623 | A |   | 2/1966 | Rector |   |
| 3,748,705 | A |   | 7/1973 | Deaton et al. |   |
| 4,966,365 | A |   | 10/1990 | Winston |   |
| 5,257,983 | A | * | 11/1993 | Garyantes et al. | 604/403 |
| 5,375,278 | A |   | 12/1994 | VanWinkle et al. |   |
| 5,829,079 | A |   | 11/1998 | Castro |   |
| 5,891,070 | A |   | 4/1999 | Shirouzu et al. |   |
| 6,470,705 | B2 |   | 10/2002 | Bride-Flynn |   |
| 6,561,958 | B2 |   | 5/2003 | Pappert |   |
| 6,582,383 | B2 |   | 6/2003 | Horning |   |
| 6,725,511 | B1 |   | 4/2004 | Rodseth |   |
| 2003/0115670 | A1 |   | 6/2003 | Antinoro |   |

* cited by examiner

Primary Examiner—Tatyana Zalukaeva
Assistant Examiner—Ginger T Chapman
(74) Attorney, Agent, or Firm—The Webb Law Firm (57) ABSTRACT The present invention provides an embalming weighted positioning device for maintaining and/or restoring a cadaver in a substantially normal lifelike appearance before, during, and after the embalming process, comprised of a flexible, conformable adherent container that allows for the nesting of two or more containers. The container can have a fill spout with a removable cover for filling or emptying the container with particulates and/or air before, during or after the embalming process. Also provided is a method for maintaining and/or restoring the body parts of a cadaver to a substantially normal lifelike appearance by controlling body fluid deposition in the body of a cadaver, and by positioning the body parts of a cadaver before, during and/or after the embalming process, by placing at least one container on top of, under or next to a body part of the cadaver.

21 Claims, 6 Drawing Sheets

METHOD OF EMBALMING WITH SAND-FILLED WEIGHTS

CROSS REFERENCE TO RELATED APPLICATION

The present application claims priority to U.S. Provisional Application No. 60/577,653, filed Jun. 7, 2004, which is incorporated by reference herein.

BACKGROUND OF THE INVENTION

1. Field of the Invention

The present invention relates to the art of embalming. More particularly, the present invention relates to methods for maintaining and/or restoring the appearance of a cadaver to as near lifelike proportions and contours as possible.

2. Description of Related Art

In the embalming arts, one of the more difficult problems confronting the embalmer in preparing a cadaver for final appearance is to give the exposed areas of the body lifelike qualities either by preserving the appearance of a body which has not suffered matter changes prior to death or by restoring the features of the body which have undergone distortion, emaciation or swelling prior to death to as near the original normal condition as possible.

Many difficulties may arise in positioning a body as embalming fluids are injected as the initial stiffness of the muscles due to rigor mortis leaves. The embalming fluids create a final firmness and stiffening of the body after injection, but other processing of the cadaver needs to be done as well, such as forming the cheeks and lips with various products, so that the mortician frequently is unable to satisfactorily position each portion of the body as it sets in firmness. This typically results in unforeseen and unnatural positions of the body, particularly head, limb and finger positions, which is a source of much extra work and effort to resoften the limb or other portion of the body.

Furthermore, a body in a posthumous state typically suffers from edema, i.e., swelling, especially in the face and the extremities. Edema is an excessive accumulation of fluid that has entered the body tissues from the circulation. The resultant swelling may be local, associated with an injury or inflammation, or general, as occurs in heart or kidney failure. The degree and location of swelling varies depending on the particular cadaver and cause of death. For example, swelling can be caused by events that occur prior to or after death, such as congestive heart failure, intravenous fluid intake, poor circulation, organ transplantation, kidney failure, renal failure, or swelling from the embalming process because of impedance due to blood clots or from the embalming process itself.

Current techniques used to handle the above-described difficulties have been to position body parts of the cadaver with the use of blocks, but they have proved difficult to handle and blocks of many sizes and heights need to be provided, with no single block sufficing in all cases, because of the unequal firming of the various portions of the body. Further, blocks and other positioning devices typically cause some degree of pinching or distortion of the body parts contacted.

Other techniques typically used to reduce pitting edema include the use of cold water on cotton that is pressure applied to a body part; special embalming fluid; aspiration of the excess body fluid; elevation of the extremities; application of towels or straps, such as to the neck area; rubber water collars; plastic pneumatic collars; and tissue drying via heat application.

Additionally, obese cadavers present special problems because oftentimes they are in an excessively edematous condition, so that when the body reclines at death, the weight of the flesh causes it to hang down in unnatural, unlifelike positions that are especially difficult to correct during the embalming process.

None of the above techniques has been shown to solve adequately the above-described problems that are encountered when a mortician endeavors to maintain and/or restore a normal, lifelike appearance to the deceased person in preparation for the final viewing.

Thus, a need exists for an improved body positioning device and method that can be used before, during, and after the embalming process in order to maintain and/or restore a cadaver to a conformation substantially normal to lifetime appearance before, during, and after the embalming process.

SUMMARY OF THE INVENTION

The object of the present invention is to provide a body positioning device for maintaining and/or restoring a substantially normal, lifelike appearance to the body parts of a cadaver before, during, and after the embalming process, while at the same time avoiding the undue application of pressure that can cause unnatural distortion of the body tissues.

Yet another objective of the present invention is to provide a method for controlling body fluid and/or embalming fluid deposition before, during, and after the embalming process in order to maintain a substantially normal, lifelike appearance to the body parts of a cadaver.

These and other objectives of the present invention are achieved by providing an embalming weight for maintaining and/or restoring a cadaver in a substantially normal lifelike appearance before, during, and/or after the embalming process, comprised of a particulate-filled container with ends and/or sides that may be either concave-shaped or convex-shaped. Additionally, the weight may have a covered fill spout defining an opening extending through the surface of the container, preferably in the front side or back side of the container for filling or emptying the container with the particulate matter and/or air. Alternatively, the weight may include a valve positioned on a surface of the container through which the opening extends. The valve may be pushed into the opening to prevent the particulate matter and/or air from escaping from the opening. The particulate-filled container can be manufactured in various shapes, sizes and weights to accommodate different body areas as well as to conform to the individual size, weight and form of a cadaver.

Also provided is a method for maintaining and/or restoring the body parts of a cadaver to a substantially normal lifelike appearance by controlling body fluid deposition in the body of the cadaver, and by positioning the body parts of a cadaver before, during and/or after the embalming process, comprised of placing at least one particulate-filled embalming weight on top of, under or next to the body part of the cadaver.

DETAILED DESCRIPTION OF THE INVENTION

The present invention provides a method and device for maintaining and/or restoring a cadaver to a substantially normal, lifelike appearance before, during and/or after the embalming process. In general, the device includes an embalming weight for positioning atop of, adjacent to or beneath a cadaver. The mass of the embalming weight exerts pressure on the cadaver and the fluids therein to control the amount of fluid present in the portion of the cadaver contacted by the embalming weight. While the present invention is described as an embalming weight since the device may be used during embalming to control the flow of embalming fluids, this is not meant to be limiting. The device may also be used to readjust the orientation of body parts prior to embalming. In addition, the present invention may be used to maintain body part position and/or control fluids for presentation of the cadaver during a funeral viewing or the like.

For purposes of the description hereinafter, the terms "upper", "lower", "right", "left", "vertical", "horizontal", "top", "bottom" and derivatives thereof shall relate to the invention as it is oriented in the drawing figures. However, it is to be understood that the invention may assume various alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

In one embodiment of the invention shown in FIGS. 1-4, an embalming weight 2 includes a container 15 that may be produced from flexible, conformable, adherent plastic matter. The container 15 may be in the configuration of a bag having a front surface 4, a back surface 6, two sides 8 and 10, and two ends 12 and 14. By "bag" it is meant a container that may receive particulate matter and/or air.

Figure 2:
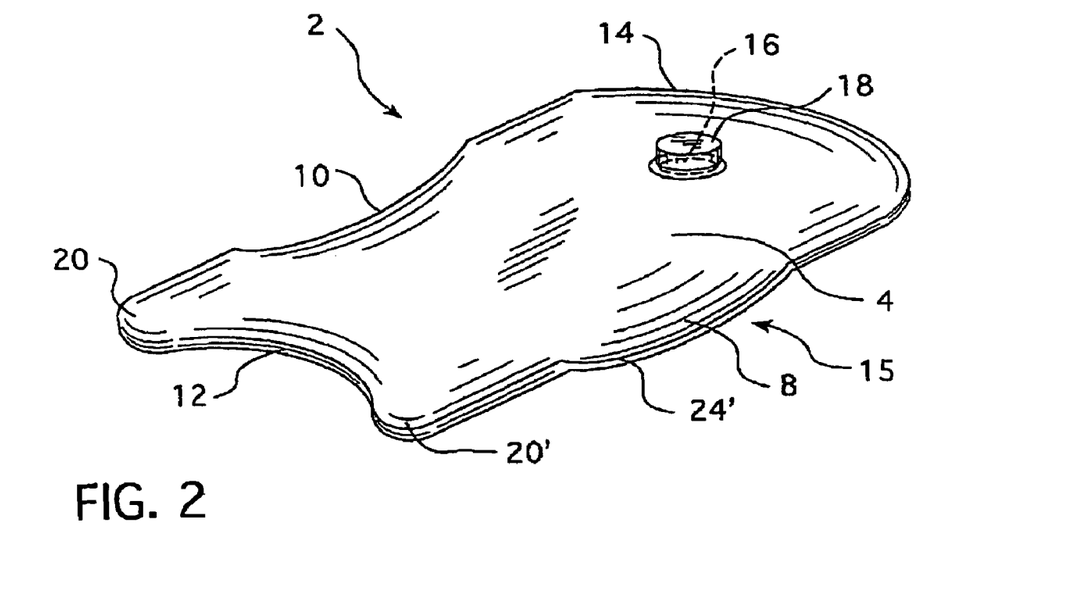
FIG. 2 is a perspective view of an embalming weight showing an opening therein, a fill spout and a cap.
Figure 2A:
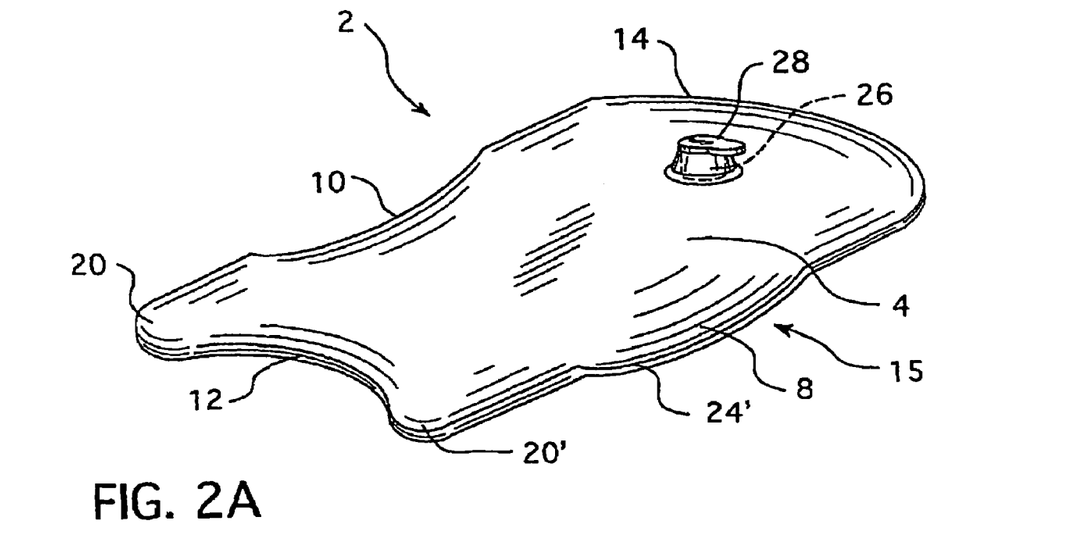
FIG. 2A is a perspective view of the embalming weight of FIG. 2 showing an opening therein with a valve and a cap.
Figure 3:
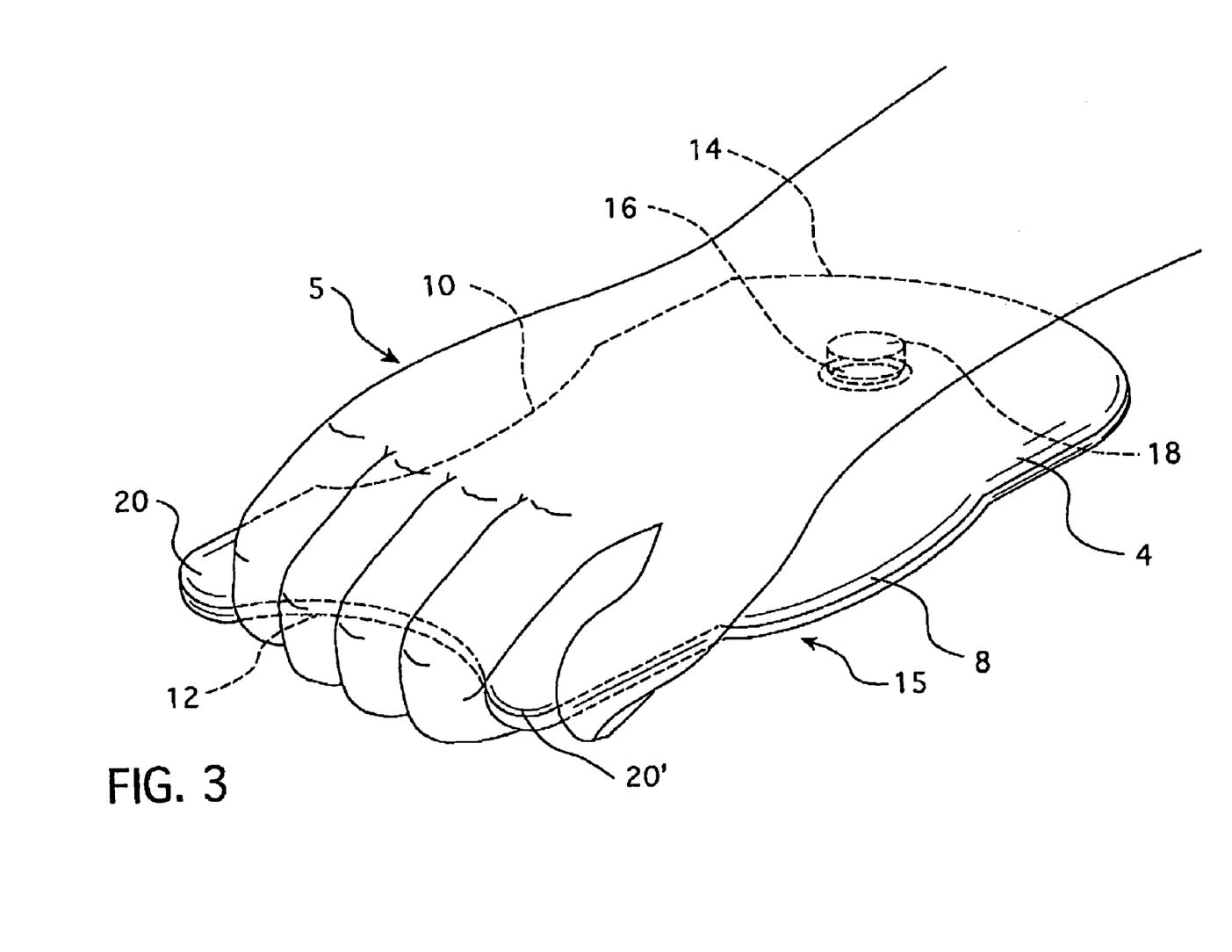
FIG. 3 is a plan view of an embalming weight container with a hand placed atop the container showing the fingers positioned thereon and the thumb positioned thereover.
Figure 4:
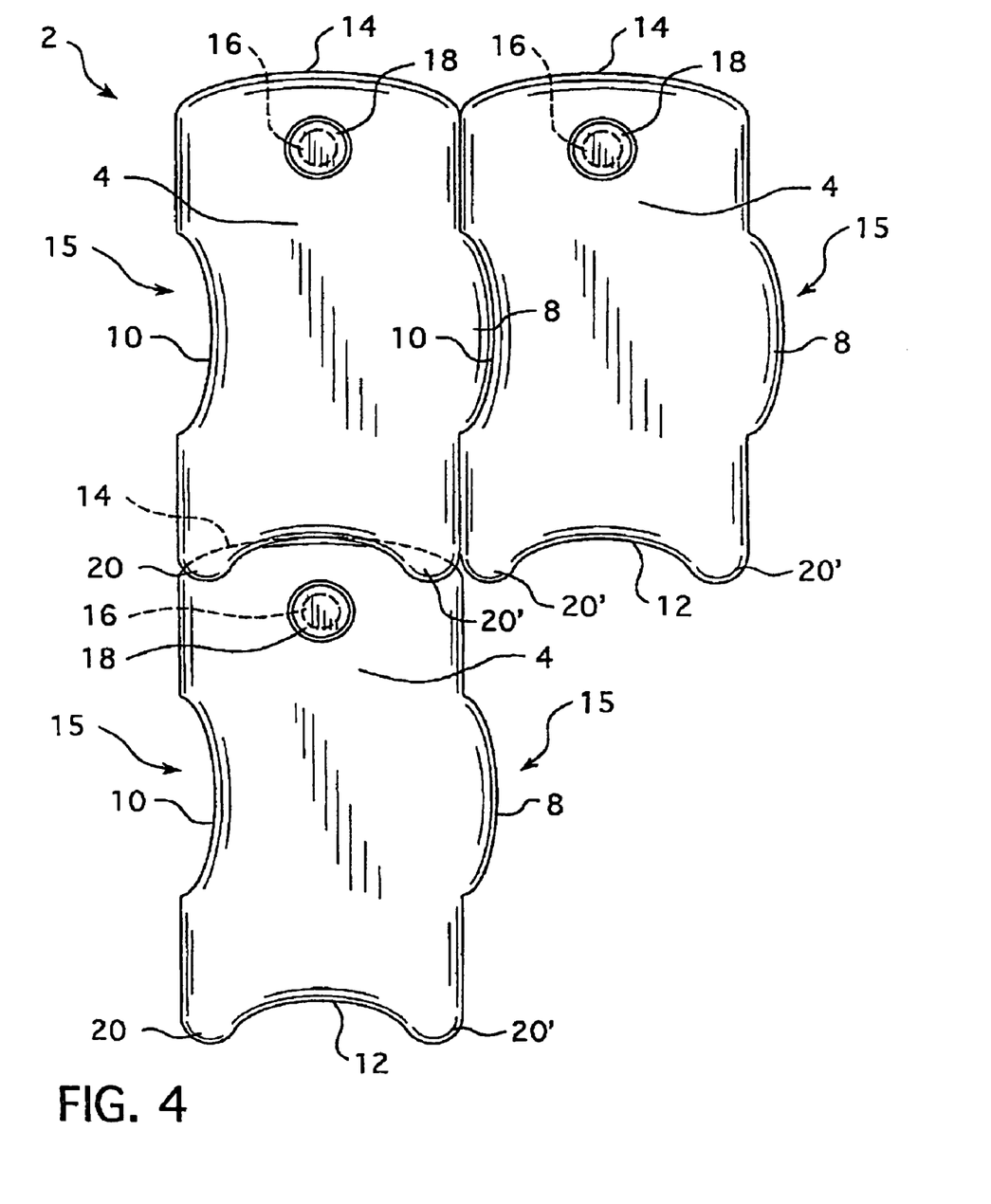
FIG. 4 is a plan view showing an arrangement of three embalming weights.

In one embodiment, one side 8 of the container 15 is convex-shaped and the other side 10 is concave-shaped, and one end 12 of the weight 2 is concave-shaped and the other end 14 is convex-shaped (FIGS. 1-4). The concave-shaped sides 10 and ends 12 of one weight 2 allows for each weight 2 to be nested adjacent to the convex-shaped sides 8 and ends 14 of another weight 2 (FIG. 4). Additionally, the concave shape of one end 12 is particularly useful in positioning a cadaver hand. For example, the palm of a hand 5 may be placed on the front surface 4 with the fingers curving in a natural configuration around the concave end 12. Thumb support members (20, 20') can provide support for the thumb (FIG. 3). The front surface 4 and the back surface 6 (FIG. 1A) of the weight 2 may be joined together at the sides 8, 10 and ends 12, 14 by various techniques known in the art for bonding plastics, such as, without limitation, heat seaming or radio frequency welding. Other configurations for the sides 8 and 10 and ends 12 and 14 of the container 15 can be employed in the present invention, such as, for example, straight sides and ends.

The container 15 receives particulate matter 22 such as sand or other finely granulated matter. While sand is described for use with the present invention, any other suitable particulate matter can be used in the present invention provided that it is flowable into the container 15 and moveable therein. The embodiments of the present invention described and shown herein include a single structure for filling and removing particulate matter from a container. This is not meant to be limiting as a plurality of such structures may be used.

Figure 1:
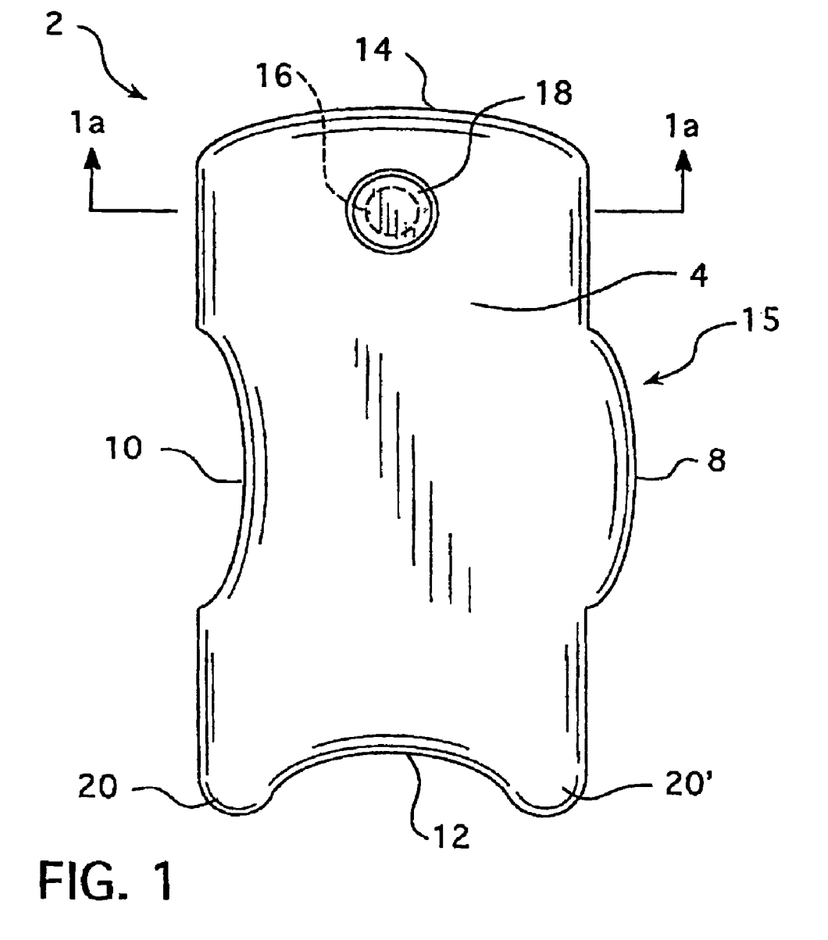
FIG. 1 is a plan view of an embalming weight of the present invention.
Figure 1A:
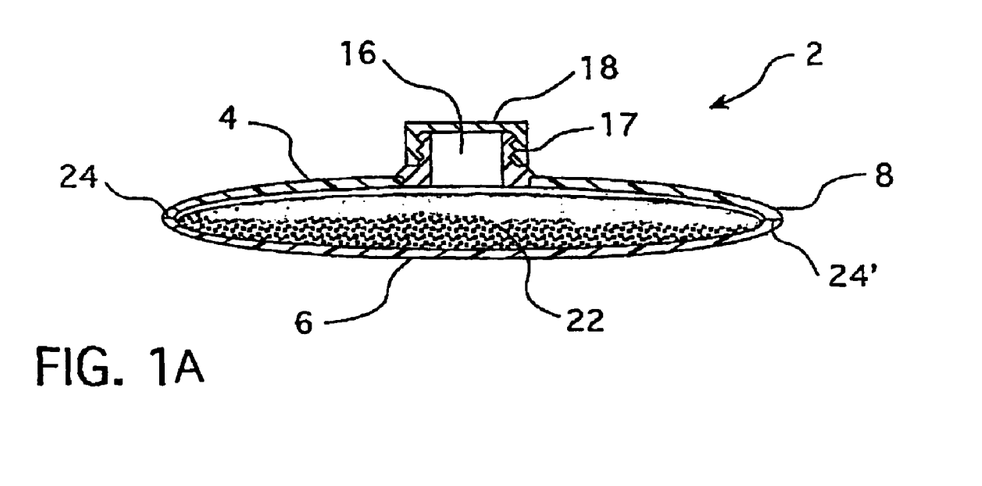
FIG. 1A is a cross-sectional view of the embalming weight shown in FIG. 1.

As shown in FIG. 1A, the weight 2 has a fill spout 17 defining an opening 16 extending through a surface of the container 15, preferably the front surface 4 or the back surface 6, which is used for filling or emptying the container with particulate matter 22 and/or air before, during and/or after the embalming process. The fill spout 17 may include a removable cover 18 that closes the opening 16, such as a cap, threadably inserted thereon. Other closure mechanisms may be used such as a fill spout with a snap fit cover.

In an alternative embodiment, as shown in FIG. 2A, the weight 2 has a conventional valve 26 commonly found in recreational balls which defines the opening 16 extending through the surface of the container. The valve 26 includes a plug that may be pushed into the opening 16 after filling or emptying the weight 2 with particulate matter and/or air in order to prevent the particulate matter and/or air from escaping. Thus, it is contemplated that the weight 2 of the present invention can have one or more structures for resealably closing the opening 16 through a surface of the container 15 such as the fill spout 17 with a cover 18 preferably threadably inserted therein or a valve 26 with a cover 28 preferably snapped thereon or both. Other resealable closure structures may be used in the present invention, the forgoing being examples thereof, provided such structures are configured for receiving particulate matter 22 therethrough for adjusting the fill level of particulate matter 22 in the container 15.

The weight 2 may be manufactured in various sizes to accommodate different sized cadavers and different body parts. For example, smaller containers can be made for the special requirements encountered with children or infant cadavers, and larger containers can be made for large or obese cadavers.

The weight may be of various shapes, such as, without limitation, rectangular-shaped, square-shaped, triangular-shaped, round, or variably shaped to fit a particular body region, such as the face or eyes. Additionally, the weight 2 may be of varying mass depending on the mass needed to optimally bear down and/or position the particular body part. The mass of the weight 2 can be adjusted by adjusting the fill level of particulate matter 22 in the container 15. Thus, the weight 2 of the present invention may be customized to conform to the particular size and dimensions of a cadaver. For example, the mass of the weight 2 may be varied, i.e., made lighter or heavier, by removing sand and adding air or replacing air with more sand, respectively. Additionally, sand may be added or removed via the fill spout 17 or valve 26 to customize the mass of the weight 2 before, during or after the embalming process as needed.

The present invention also provides a method for controlling body fluid deposition in the body of a cadaver before, during and after the embalming process, comprised of positioning at least one weight 2 as described above on top of, under, or next to a body part of the cadaver in order to maintain and preserve the cadaver in a substantially normal lifelike appearance. Control of body fluid may be achieved in the present invention by placing the weight 2 on top of a body part in need of fluid control, e.g. an edematous portion of a cadaver. Pressure exerted by the weight 2 on the body part urges body fluid away from that body part to reduce the swelling thereof or prevent swelling thereof during or after embalming. The amount of particulate matter within the weight 2 may be adjusted (through the opening 16) to control the amount of pressure exerted on a cadaver. Elevation of a body part may also contribute to fluid control, and the weight of the present invention may be used to prop up a body part. The weight of the present invention may also be used to prop or support a body part into a lifelike position, with or without concomitant body fluid control. As such, the weight of the present invention can be used for displaying a body for a funeral viewing. It will be appreciated that the weight of the present invention may be used for a variety of purposes before, during and/or after embalming a cadaver. The term weight is not meant to limit the present invention to an article that exerts its mass onto a cadaver, although that function is contemplated herein.

The particulate matter, e.g. sand, within the container of the weight is particularly suited for conforming the weights to the contours of a cadaver. The particulate matter readily flows within the container allowing for adjustment of pressure applied to a cadaver. Particulate matter can be added to the container to increase the pressure applied to a cadaver so as to control fluids within the cadaver in the region of the weight. Likewise, upon placement of a weight, it may be determined that less pressure on the cadaver is needed, and the particulate matter may be removed from the container to reduce the pressure applied to a quavered. Excessive pressure could result in unlifelike features of the cadaver. Particulate matter also allows for various portions of the weight to exert greater pressure. For example, a weight applied to an arm may require less pressure directly on the upper side of the forearm, yet additional pressure is needed along the sides of the forearm. The particulate matter within the weight can be moved by manipulating the quantity of particulate matter in portions of the weight before or after the weight is applied to the cadaver. When the weight of the present invention is used as a support, such as beneath a cadaver, air may be added to the container to create added volume to the weight without increasing the mass of the weight.

A feature of the present invention is the flexibility and conformability of the container 15. To this end, it is contemplated that the containers of the present invention be manufactured from any suitable plastic composition, such as, without limitation, polyvinyl chloride or polypropylene. Additionally, the plastic composition can contain one or more softening agents, which include, without limitation, phthalates, such as di-ethylhexyl-phthalate (DEHP). The combination of plastic and softening agent confers surface adhesion properties to the container 15 so that the container 15 can be placed in many positions relative to a cadaver, as well as adjacent to another container 15, and adhere to the surface it contacts without easily sliding away or separating therefrom. As shown in FIG. 4, when the weights 2 are positioned side by side by aligning the concave-shaped side 10 of one weight 2 adjacent to a convex-shaped side 8 of another weight 2 and the concave-shaped end 12 of one weight 2 adjacent to the convex-shaped end 14 of another weight 2, the complementary-shaped nature of the weights 2 allows for the weights 2 to be nested together without easily separating. Additionally, the weights 2 can be placed atop one another without slipping to provide additional weight-bearing force when needed, for example when positioning obese cadavers. Furthermore, the plastic composition of the container 15 allows for easy cleaning and sanitizing, and thus the weights 2 can be used multiple times, which increases cost-effectiveness.

It will be appreciated that many of the features of the weight 2 described herein are applicable to the various embodiments of the present invention, such common features including but not limited to the inclusion of particulate matter and fill structure(s), the composition of the container, and various shapes and configurations of the containers and portions thereof.

Figure 5:
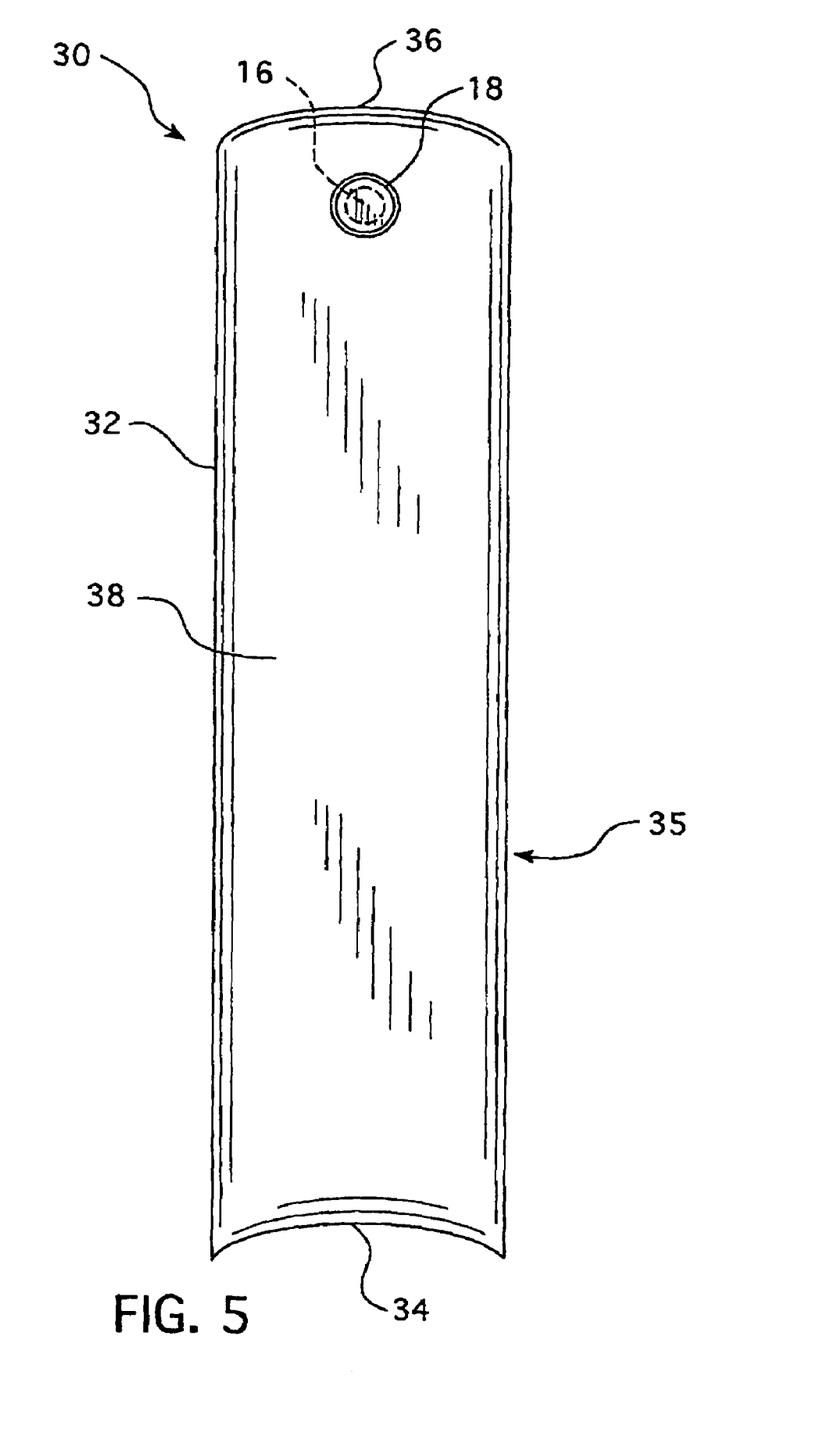
FIG. 5 is a plan view of an elongated embalming weight that can be positioned over the neck area of a cadaver.

The weight of the present invention can be used before, during or after the embalming process to maintain or restore the normal, lifelike appearance of the deceased person that has become edematous in various body areas by positioning the flexible particulate-filled container onto or under the swelled area. For example, in another embodiment of the present invention, as shown in FIG. 5, a weight 30 includes a container 35 (receiving particulate matter, not shown) with an upper surface 38 through which opening 16 is defined, container 35 having an elongated tubular shape with mostly straight sides 32, a concave-shaped end 34 and a convex-shaped end 36. Weight 30 is particularly suited for wrapping around the neck of a cadaver, however it may be used on other body parts.

Figure 6:
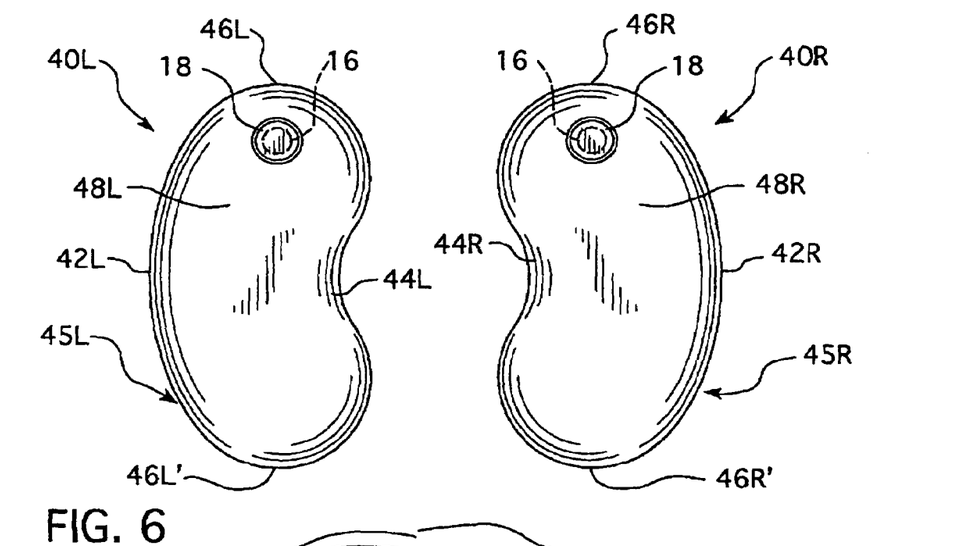
FIG. 6 is a plan view of two embalming weights conformed to fit over the cheek area of a cadaver.
Figure 7:
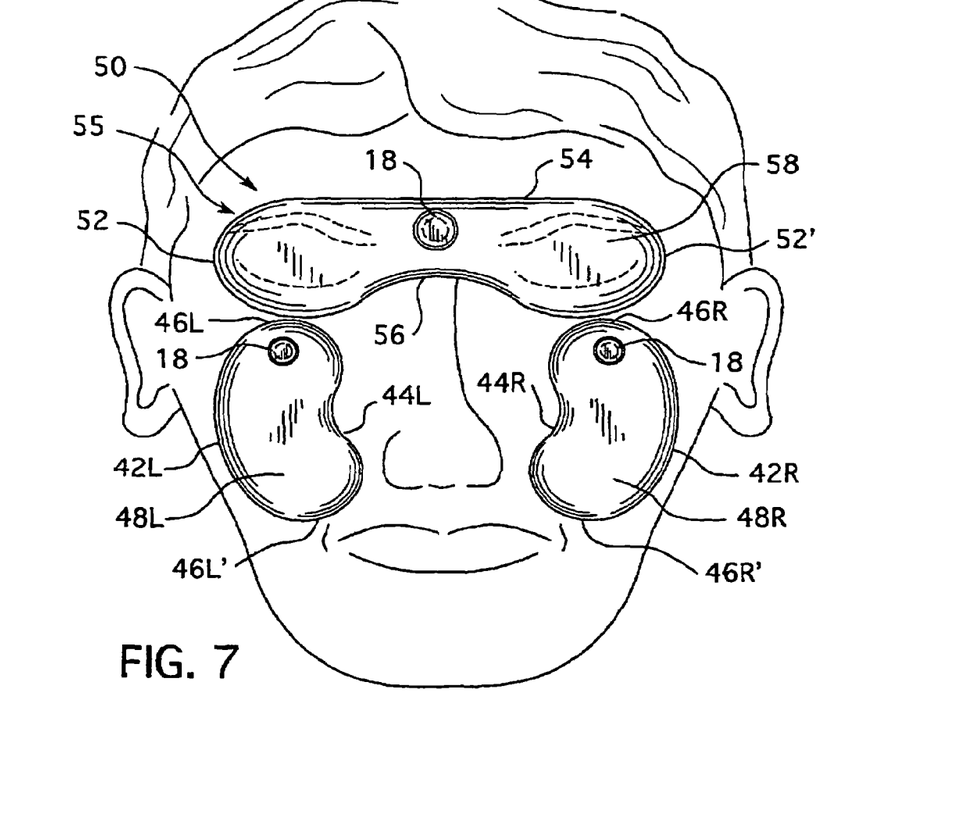
FIG. 7 is a plan view of a facial embalming weight shaped similar to a facial mask that can be positioned over the eyes and two C-shaped embalming weights that can be positioned over the cheek area of a cadaver.

In a further embodiment, as shown in FIGS. 6 and 7, weights 40L, 40R may be mirror images of each other and include containers 45L, 45R each receiving particulate matter that have respective convex ends 46L, 46L', 46R, 46R', concave sides 44L, 44R and convex sides 42L, 42R. An opening 16 (covered by a cap 18) is defined in the front surface 48L, 48R of the weights 40L, 40R. In one embodiment, containers 45L, 45R are kidney-shaped. The shape of the containers 45L, 45R is not meant to be limiting but is configured for use in covering the cheeks and cheekbone areas of a cadaver to lessen swelling thereof, as shown in FIG. 7. Also shown in FIG. 7 is another embodiment of the invention of a weight 50 that is configured to cover the eye area and nose bridge of a cadaver similar to a facial mask, such configuration shown not being limiting. Weight 50 includes a container 55 (containing particulate matter), convex ends 52, 52', a straight side 54 and a concave side 56 which may be placed atop the area of a cadaver to lessen swelling thereof. An opening 16 (covered by a cap 18) is defined in the front surface 58 of the weight 50.

Hence, the weights of the present invention (including the particular embodiments described as weights 2, 30, 40, and 50) can be used to control excess swelling due to fluid retention, i.e., edema, such as pitting edema, and deformation of body parts prior to, during and after embalming. Such swelling and deformation of the body parts of a cadaver typically are encountered if the deceased person suffered from congestive heart failure, kidney failure, renal failure or poor circulation while alive. Edema also can occur from retention of intravenous fluid or the formation of a blood clot during the embalming process. Thus, the weights of the present invention can be placed under a body area, such as the legs, to elevate that area for a period of time to aid in displacing the edematous fluid away from the swollen region. Additionally, the proportion of particulate matter to air within the weights can be varied in order to more closely conform to the particular body area.

The weights of the present invention are particularly suited for positioning body parts that have undergone contortions. For example, the weights can be placed as shoulder blocks to straighten the upper torso and shoulder regions that have contorted due to osteoporosis, scoliosis, arthritis or obesity. Similarly, the weights can be placed adjacent to the hip region to straighten the lower torso.

Extremities have a tendency to distort in unnatural conformations, e.g., one digit pointing outwardly from the rest of the hand. As shown in FIG. 3, the weights of the present invention can be used to confine the fingers together in a natural pose by placing the palm of a hand 5 which has become stiff from rigor mortis over a weight 2, bending the first four fingers over and around the concave-shaped end 12 of the weight 2 and bending the thumb of the hand 5 over and around the thumb tab 20 of the concave-shaped end 12 of the weight so as to conform the hand 5 to a more lifelike appearance. Larger extremities, such as arms and legs may be aligned into a natural position prior to, during or after the embalming process and maintained in that position by placing the weights of the present invention of appropriate size and mass next to, under or on top of the extremities.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

The invention claimed is:

1. A flexible, conformable, adherent device for maintaining and preserving a cadaver in a substantially normal lifelike appearance before, during, and/or after the embalming process, comprising:
   a container having a resealable opening defined in a surface of said container, wherein said opening is configured to fill and/or empty said container with particulate matter; and
   granulated matter received and positionable within said container, such that said device is manipulatable to control fluids within a cadaver and achieve a lifelike appearance of the cadaver when applied directly onto the cadaver by exerting pressure onto the cadaver.

2. The flexible, conformable device of claim 1, wherein said container further comprises a closure structure closing said opening, such that the mass of said container is variable by adding or removing said particulate matter and/or air through said opening.

3. The flexible, conformable device of claim 1, wherein one side of said container is convex-shaped and another side of said container is concave-shaped.

4. The flexible, conformable device of claim 1, wherein one end of said container is concave-shaped and another end of said container is convex-shaped.

5. The flexible, conformable device of claim 1, wherein said container includes a thumb support member.

6. The flexible, conformable device of claim 1, wherein the shape of the container is configured to fit a particular body region of a cadaver.

7. The flexible, conformable device of claim 6, wherein said container is elongated with straight sides and has one concave-shaped end and one convex-shaped end for positioning around the neck of a cadaver.

8. The flexible, conformable device of claim 6, wherein said container is in the configuration of a mask for positioning said container atop the eyes of a cadaver.

9. The flexible, conformable device of claim 1, wherein said container is configured for positioning atop a cheek of a cadaver.

10. The flexible, conformable device of claim 1, wherein said container is comprised of a flexible, adherent plastic composition selected from the group consisting of polyvinyl chloride and polypropylene.

11. The flexible, conformable device of claim 10, wherein the plastic composition contains a phthalate compound such as di-ethylhexyl-phthalate.

12. The flexible, conformable device of claim 1, wherein said container further comprises a front surface and a back surface, said front surface and said back surface joined together by heat seaming or radio frequency welding.

13. A method for controlling internal fluid deposition in the body of a cadaver before, during and/or after an embalming process, comprising:
   positioning at least one flexible, conformable device on top of, under or next to a body part of a cadaver in order to maintain and preserve the cadaver in a substantially normal lifelike appearance, said device comprising a container and particulate matter received within said container, said container including a resealable opening defined therein; and
   adjusting the quantity of particulate matter and/or air within said container to control pressure exerted on the cadaver by emptying or filling said container with particulate matter and/or air through the resealable opening.

14. The method of claim 13, wherein one side of said container is convex-shaped and another side of said container is concave-shaped.

15. The method of claim 13, wherein one end of said container is concave-shaped and another end of said container is convex-shaped.

16. The method of claim 13, further comprising adjusting the mass of said container by filling or emptying the particulate matter from the container as needed prior to, during and/or after embalming the cadaver to obtain a desired pressure on the cadaver in order to control internal fluid deposition therein.

17. The method of claim 13, wherein at least two containers are placed adjacent each other by positioning said convex-shaped side of one container adjacent to said concave-shaped side of another container.

18. The method of claim 13, wherein at least three containers are placed adjacent each other by positioning said convex-shaped side of one container adjacent to said concave-shaped side of another container and said concave-shaped end of one container adjacent said convex-shaped end of another container.

19. The method of claim 13, wherein a palm of a hand is placed on a surface of said container with fingers of the hand curving in a natural configuration around said concave end of the container, and wherein a portion of said container provides support for a thumb of said hand.

20. The method of claim 13, wherein said container is comprised of a flexible, adherent plastic composition selected from the group consisting of polyvinyl chloride and polypropylene.

21. The method of claim 20, wherein said plastic composition contains a phthalate compound such as di-ethylhexyl-phthalate.

* * * * *